US009038225B2

(12) United States Patent
Haynes et al.

(10) Patent No.: US 9,038,225 B2
(45) Date of Patent: May 26, 2015

(54) ELECTRIC TOOTHBRUSH WITH DRIVE MECHANISM

(71) Applicant: Den-Mat Holdings, LLC, Lompoc, CA (US)

(72) Inventors: Ronald Wayne Haynes, Fairfield Bay, AR (US); Ian Thorne, Thornton, CO (US); Jered Harvey Dean, Arvada, CO (US); Emanuel Guzman, Aurora, CO (US); Sean Michael Cole, Denver, CO (US); John R. Gardner, Parker, CO (US); Scott Douglas Nelson, Denver, CO (US)

(73) Assignee: Den-Mat Holdings, LLC, Lompoc, CA (US)

( * ) Notice: Subject to any disclaimer, the term of this patent is extended or adjusted under 35 U.S.C. 154(b) by 7 days.

(21) Appl. No.: 14/068,626

(22) Filed: Oct. 31, 2013

(65) Prior Publication Data

US 2014/0115800 A1 May 1, 2014

Related U.S. Application Data

(60) Provisional application No. 61/720,894, filed on Oct. 31, 2012.

(51) Int. Cl.
*A61C 17/26* (2006.01)
*A61C 17/22* (2006.01)

(52) U.S. Cl.
CPC ............ *A61C 17/26* (2013.01); *Y10T 29/49826* (2015.01); *A61C 17/222* (2013.01)

(58) Field of Classification Search
CPC ........................................................ A61C 17/26
USPC ...................... 15/21.1, 22.1, 23, 28
See application file for complete search history.

(56) References Cited

U.S. PATENT DOCUMENTS

| 3,835,858 | A | * | 9/1974 | Hagen | 606/180 |
|---|---|---|---|---|---|
| 4,827,552 | A | * | 5/1989 | Bojar et al. | 15/28 |
| 5,054,149 | A | * | 10/1991 | Si-Hoe et al. | 15/28 |
| 5,697,117 | A | * | 12/1997 | Craft | 15/22.1 |
| 7,955,079 | B2 | * | 6/2011 | Chronister et al. | 433/125 |
| 2005/0144744 | A1 | * | 7/2005 | Thiess et al. | 15/22.1 |

* cited by examiner

*Primary Examiner* — Laura C Guidotti
(74) *Attorney, Agent, or Firm* — Den-Mat Holdings, LLC; Frederick W. Tong (57) ABSTRACT

A toothbrush that includes a brushing attachment and a handle. The brushing attachment includes a main body portion with a hollow neck having an attachment opening and a head with a cleaning member opening, a drive shaft positioned in the neck, a cleaning member drive mechanism matingly engaged with gearing on the drive shaft, and a cleaning member extending through the cleaning member opening in the head and operatively associated with the cleaning member drive mechanism. The drive shaft includes a spline drive on one end and gearing on the opposite end. The handle includes a main body portion with a brushing attachment connection receiver that is at least partially received in the attachment opening. The brushing attachment connection receiver includes a recess defined therein that receives a drive hub with a grooved recess defined therein that receives the spline drive.

5 Claims, 7 Drawing Sheets

ELECTRIC TOOTHBRUSH WITH DRIVE MECHANISM

RELATED APPLICATIONS

This application claims the benefit of U.S. Provisional Application No. 61/720,894, filed Oct. 31, 2012 and U.S. Provisional Application No. 61/720,931, filed Oct. 31, 2012, both of which are herein incorporated by reference in its entirety.

FIELD OF THE INVENTION

The present invention relates to a drive mechanism, and more particularly to a drive mechanism for an electric toothbrush.

BACKGROUND OF THE INVENTION

After a certain amount of use, the brush heads on electric toothbrushes often wear out and need to be replaced. A drive mechanism that is efficient and includes parts that are easily connectable between the new brushing attachment and handle is desirable.

SUMMARY OF THE PREFERRED EMBODIMENTS

The invention generally is a drive interface between a powered toothbrush handle that includes a battery, motor, and gear train that rotates a drive shaft located at an attachment interface, such as the attachment mechanism disclosed and claimed in pending U.S. Non-provisional patent application Ser. No. 14/068,733, filed on Oct. 31, 2013 which is incorporated herein by reference for all purposes, to power a removable brushing attachment. The drive interface includes features that help provide proper alignment during connection and drive torque during operation.

In accordance with a first aspect of the present invention there is provided a toothbrush that includes a brushing attachment and a handle. The brushing attachment includes a main body portion with a hollow neck with an attachment opening and a head with a cleaning member opening, a drive shaft positioned in the neck, a cleaning member drive mechanism matingly engaged with gearing on the drive shaft, and a cleaning member extending through the cleaning member opening in the head and operatively associated with the cleaning member drive mechanism. The drive shaft includes a spline drive on one end and the gearing on the opposite end and is positioned adjacent the attachment opening in the neck. The handle includes a main body portion that houses a motor, and a brushing attachment connection receiver extending upwardly from the main body portion that is at least partially received in the attachment opening in the brushing attachment. The brushing attachment connection receiver includes a recess defined therein that receives a drive hub therein. The drive hub includes a grooved recess defined therein that receives the spline drive. In a preferred embodiment, the grooved recess includes a straight section and an incline section, and the straight section has smaller outer diameter than the outer diameter of the incline section. Preferably, the grooved recess includes at least one drive groove having an inner surface and at least one guide groove having an inner surface, and there is clearance between the spline positioned in the guide groove and the inner surface of the guide groove. Put another way, the guide groove is larger in volume than the drive groove. In an embodiment, the grooved recess includes a plurality of alternating drive grooves and guide grooves.

In accordance with another aspect of the present invention, there is provided a brushing attachment for a toothbrush that includes a main body portion, drive shaft, cleaning member drive mechanism, and a cleaning member. The main body portion includes a hollow neck and a head, and the neck includes an attachment opening and the head includes a cleaning member opening. The drive shaft is positioned in the neck and includes a spline drive on one end and gearing on the opposite end. The spline drive is positioned adjacent the attachment opening in the neck. The cleaning member drive mechanism is matingly engaged with the gearing on the drive shaft, and the cleaning member extends through the cleaning member opening in the head and is operatively associated with the cleaning member drive mechanism. In use, motivating rotational force imparted to the spline drive is translated from the drive shaft to the cleaning member drive mechanism and to the cleaning member such that the cleaning member rotates. In a preferred embodiment, the spline drive includes a plurality of splines that each have an inclined surface on the distal end thereof. Preferably, each of the six splines includes two opposing longitudinally extending surfaces that taper toward the distal end.

The invention, together with additional features and advantages thereof, may be best understood by reference to the following description.

DETAILED DESCRIPTION OF THE PREFERRED EMBODIMENTS

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments.

Reference in this specification to "one embodiment" or "an embodiment" means that a particular feature, structure, or characteristic described in connection with the embodiment is included in at least one embodiment of the-disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "upper," "lower," "side," "short," "long," "up," "down," and "below" used herein are merely for ease of description and refer to the orientation of the components as shown in the figures. It should be understood that any orientation of the components described herein is within the scope of the present invention.

Referring now to the drawings, which are for purposes of illustrating the present invention and not for purposes of limiting the same, FIGS. 1-6 show an electric toothbrush 10 having a handle 12 and a brushing attachment 14 and that includes a drive mechanism or interface 16. It will be understood that the electrical components of the handle 12, (e.g., the motor 17, battery, etc.) and the components for transmitting motion (e.g., rotational motion) to the drive mechanism 16 are known. Therefore, a discussion of these components will be omitted. Furthermore, any type of attachment mechanism for securing the brushing attachment 14 to the handle 12 is within the scope of the present invention and, therefore, a description herein will be omitted. For example, the attachment mechanism taught in U.S. Pat. No. 8,196,246, the entirety of which is incorporated herein be reference, can be used.

Figure 1:
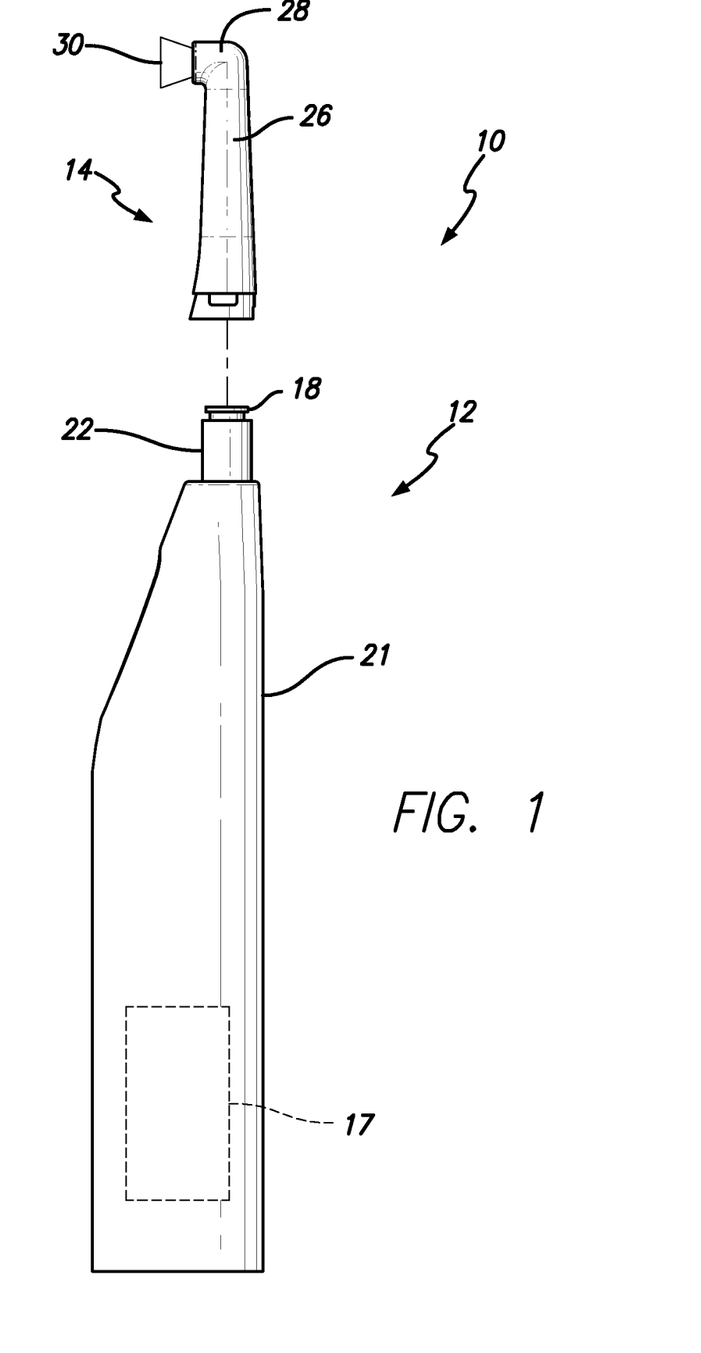
FIG. 1 is a side elevational view of an electric toothbrush having a handle and brushing attachment removably connected to one another in accordance with a preferred embodiment of the present invention.
Figure 2:
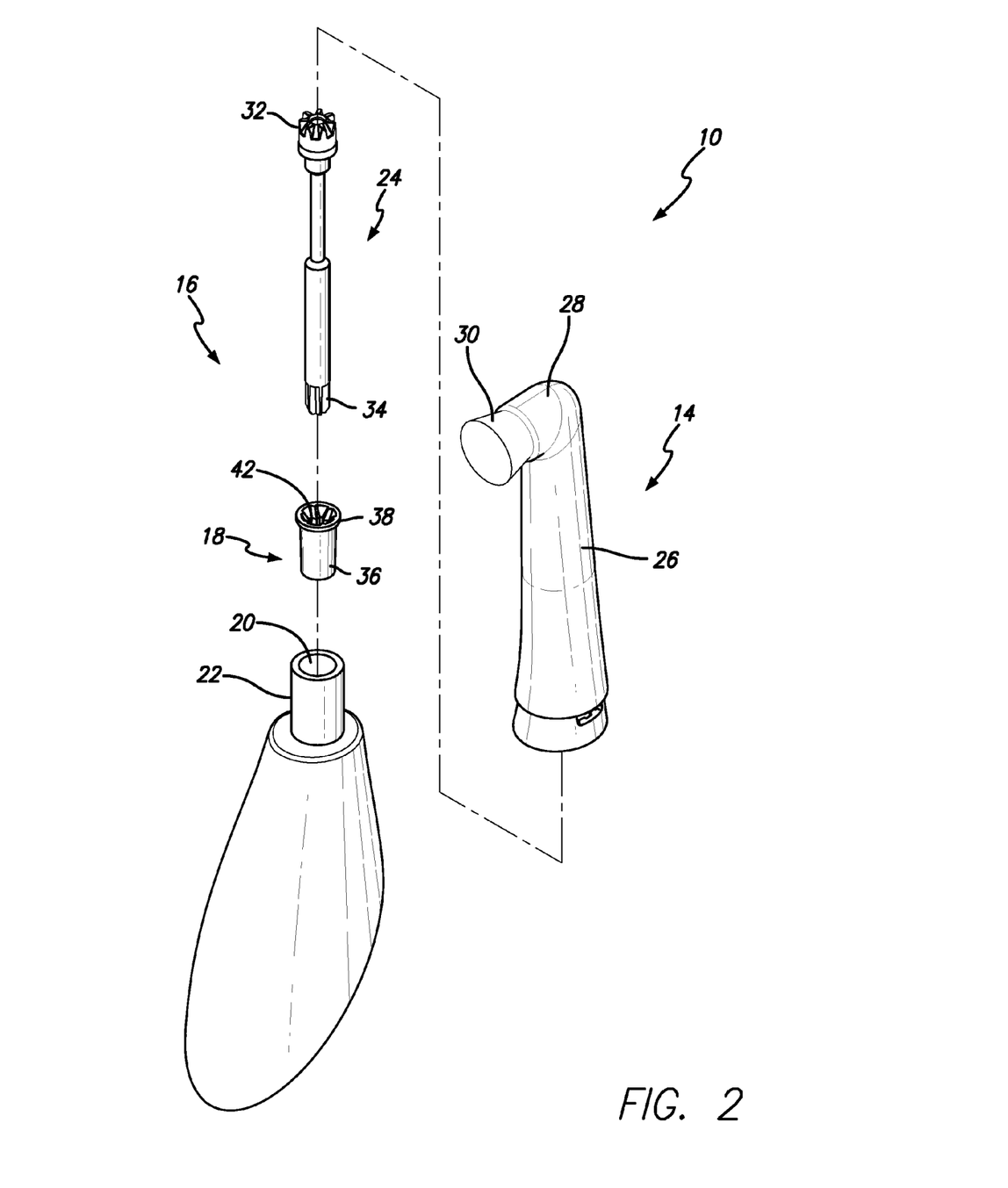
FIG. 2 is an exploded view of the electric toothbrush of FIG. 1, showing the drive hub and drive shaft.
Figure 5:
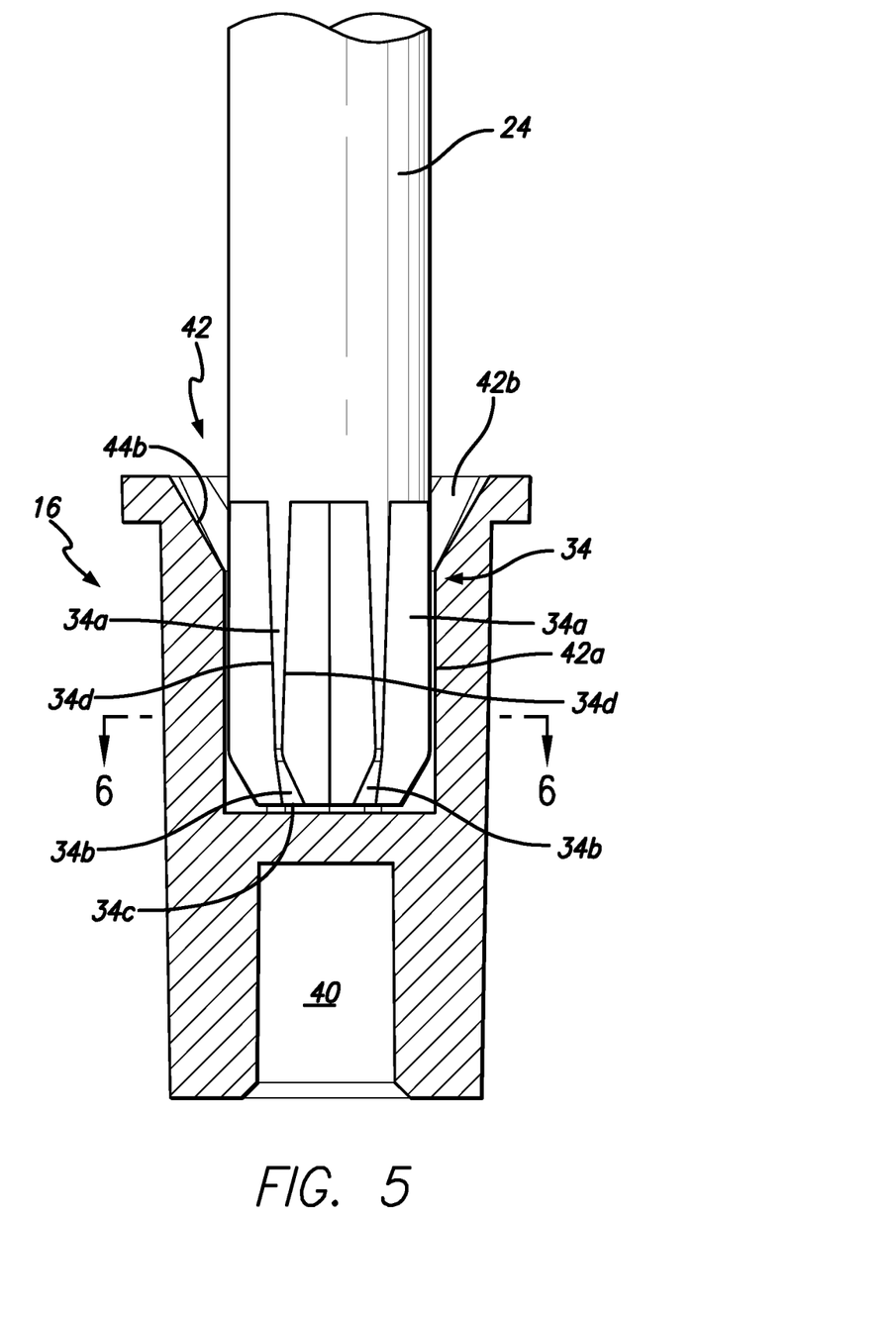
FIG. 5 is a side elevational view of the drive shaft inserted into the drive hub, with the drive hub shown in cross-section.

As shown in FIGS. 2 and 5, the drive mechanism 16 generally includes a drive hub 18 that is received in a recess 20 defined in a brushing attachment connection receiver 22 that extends from the main body portion 21 of the handle 12 and a drive shaft 24 that is housed in a neck 26 of the brushing attachment 14. A bushing can be used to position or secure drive shaft 24 within neck 26. However, this is not a limitation on the present invention.

Figures 6, 7:
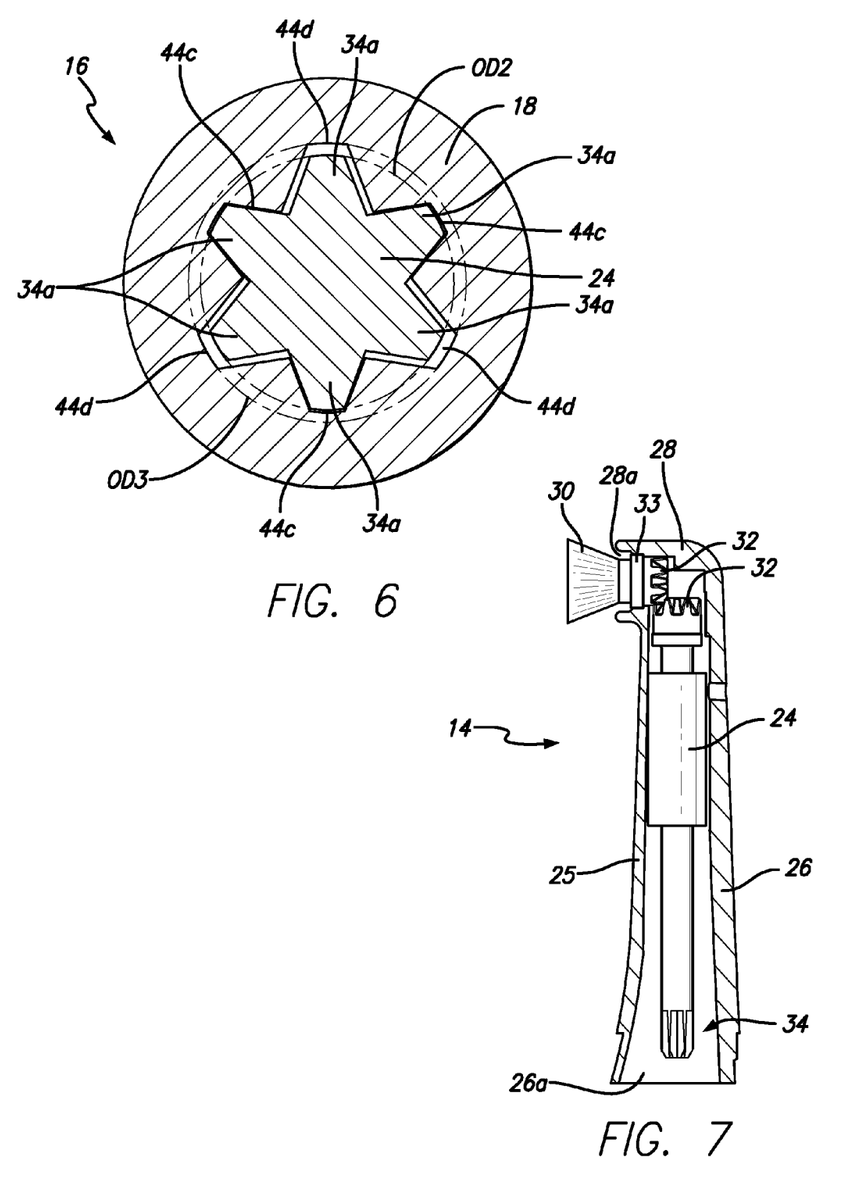
FIG. 6 is a cross-sectional view taken along line 6-6 of FIG. 5.
FIG. 7 is a cross-sectional view of the brushing attachment with the internal components in elevation.

With reference to FIGS. 2 and 7, in a preferred embodiment, brushing attachment 14 includes a main body portion 25 (comprising neck 26 and a head 28) and cleaning member 30 (e.g., bristles). The neck 26 includes an attachment opening 26a and the head 28 includes a cleaning member opening 28a. It will be appreciated by those skilled in the art, that brushing attachment 14 can include brushing surfaces other than the bristles, such as massagers, flossers or other tooth cleaning technology known in the art (these are all referred to herein generally as "cleaning members"). Internally, the brushing attachment 14 includes gearing 32 or other energy translation mechanism for translating the rotational energy through the 90 degree bend from the drive shaft 24 to the cleaning member 30.

Figure 3A:
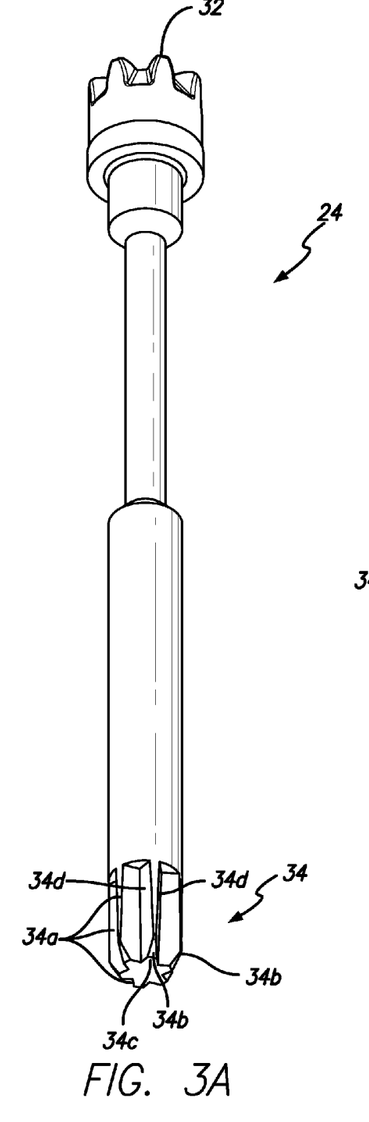
FIG. 3A is a perspective view of the drive shaft.
Figure 3B:
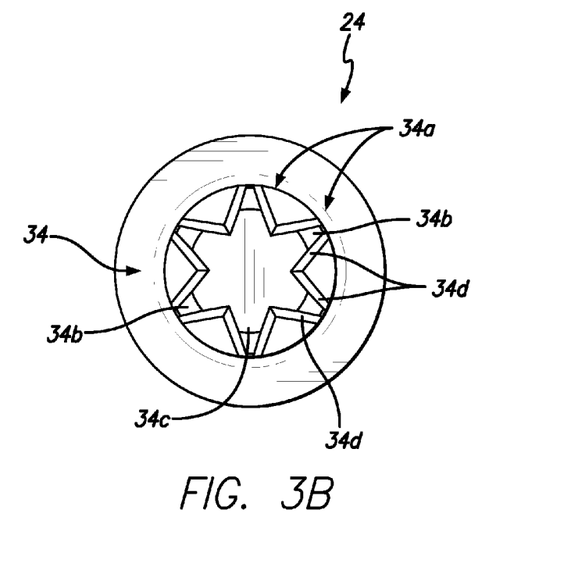
FIG. 3B is a bottom plan view of the drive shaft.

As shown in FIGS. 3A and 3B, in a preferred embodiment, drive shaft 24 is a unitary structure that includes a spline drive 34 comprising a series of splines 34a on one end thereof, and gearing 32 on the other end thereof. In another embodiment, the drive shaft 24 can be constructed of separate, non-unitary parts. As shown in FIG. 7, the gearing 32 on the end of the drive shaft 24 mates with the gearing 32 on a cleaning member drive mechanism 33 that is positioned in the head 28. Gearing for translating the rotation of the drive shaft 24 to the cleaning member drive mechanism 33 (through the 90 degree bend) and ultimately the cleaning member 30 is known. Any type of gearing or the like is within the scope of the present invention. Furthermore, any type of cleaning member drive mechanism 33 and attachment to the cleaning member 30 is within the scope of the present invention.

Figures 4A, 4B:
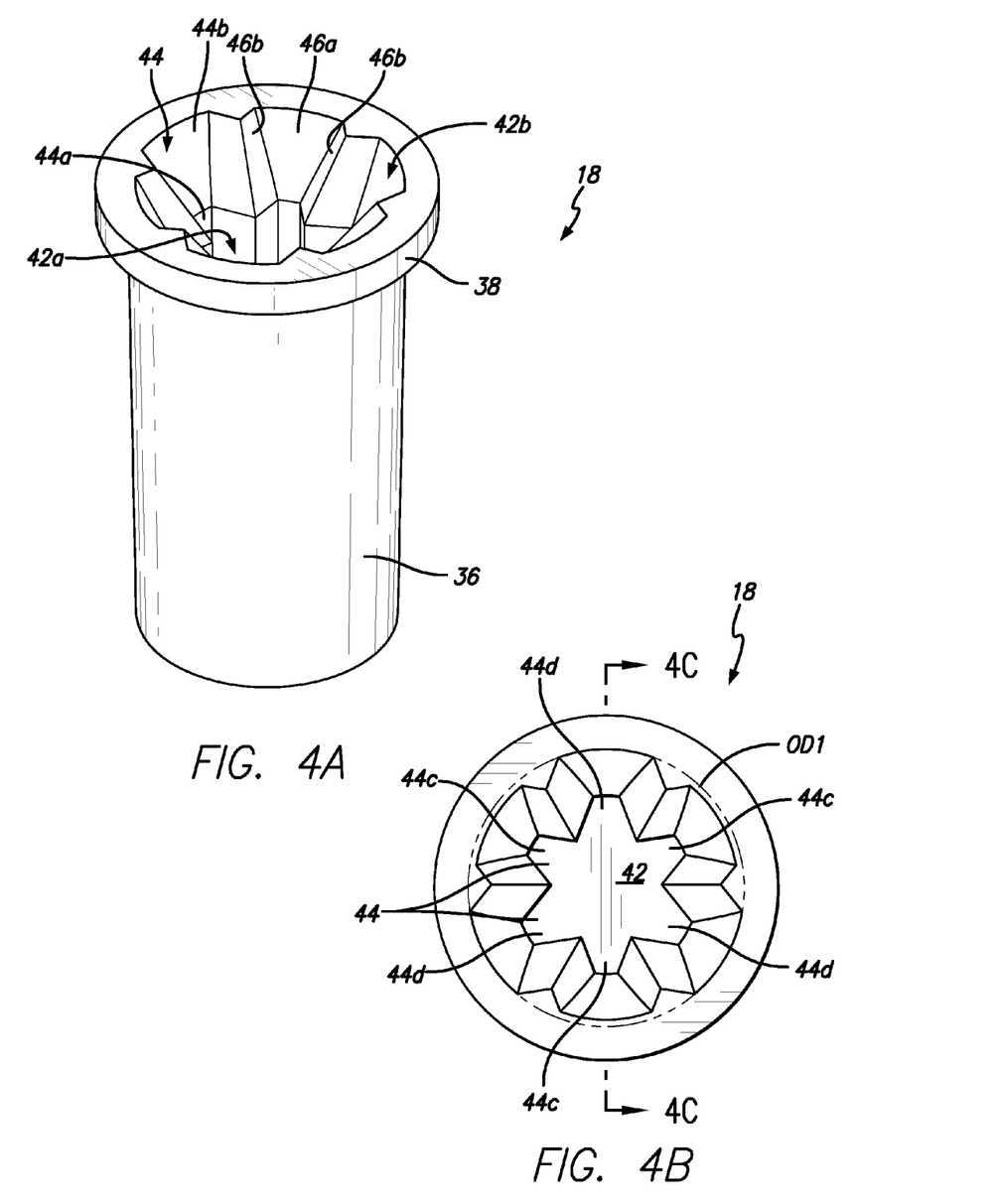
FIG. 4A is a perspective view of the drive hub.
FIG. 4B is a top plan view of the drive hub.
Figures 4C, 4D:
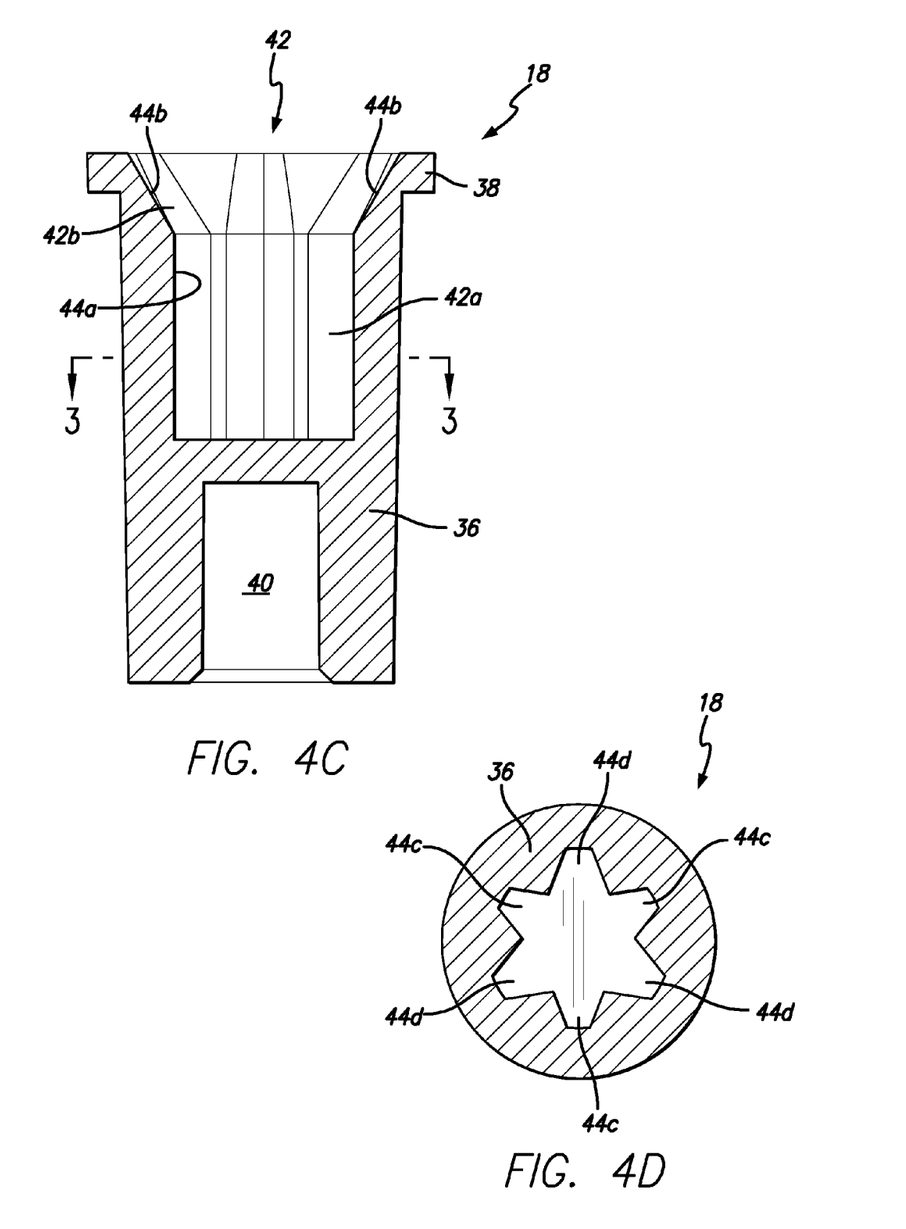
FIG. 4C is an cross-sectional view of the drive hub taken along line 4C-4C of FIG. 4B.
FIG. 4D is an cross-sectional view of the drive hub taken along line 4D-4D of FIG. 4C.

As shown in FIGS. 4A-4D, in a preferred embodiment, drive hub 18 includes a main body portion 36 that is received in recess 20, a rim 38 that seats on or is adjacent to the top surface of brushing attachment connection receiver 22, a lower recess 40 for receiving rotational energy from the motor (e.g., via a knurled shaft), and an upper or grooved recess 42 that includes a series of grooves 44 that matingly engage the spline drive 34 of the drive shaft 24. In a preferred embodiment, the grooves 44 each include a straight portion 44a and a lead in or incline portion 44b. The straight portion 44a interfaces with the splines 34a to provide the interface to facilitate the transfer of the rotational motivation generally from the handle 12 to the brushing attachment 14, and more specifically, from the drive hub 18 to the drive shaft 24. The incline portion 44b helps facilitate the insertion of the spline drive 34 into the upper recess 42. As shown in FIG. 4A, in a preferred embodiment, the incline portion 44b of the grooves 44 includes a circumferential incline surface 46a and two non-circumferential incline surfaces 46b.

The plurality of grooves 44 together form, within the upper recess 42, a straight section 42a and an incline section 42b. As shown in FIGS. 4B and 6, the incline section 42b has a greater outer diameter OD1 than the outer diameter of the spline drive 34 OD2 (measured at the tip of the individual splines 34a) and a greater outer diameter OD1 than the outer diameter of the straight section 42a OD3. The larger diameter and incline section 42b makes it easier to align the drive shaft 24 with the straight section 42a of upper recess 42 when placing a brushing attachment 14 on the handle 12. In a preferred embodiment, the splines 34a each include an inclined surface 34b on the distal end 34c thereof, which further facilitates alignment of the drive shaft 24 and drive hub 18. As is best shown in FIG. 5, the splines 34a each include two opposing longitudinally extending surfaces 34d that taper toward the distal end 34c thereof. The inclined and tapered surfaces all help facilitate mating of the spline drive 34 with the grooved opening 42 of the drive hub 18. In another embodiment, the tapered surfaces 34d and the inclined surfaces 34b can be omitted.

In a preferred embodiment, as is shown best in FIG. 4B, within the series of grooves 44, the drive hub 18 and upper recess 42 also include drive grooves 44c and guide grooves 44d. The guide grooves 44d are sized larger than the splines 34a and help provide proper alignment of the splines 34a during attachment of the brushing attachment 14. The clearance between the surfaces of splines 34a and the inner surfaces of guide grooves 44d are shown in FIG. 6. The drive grooves 44c are sized to snugly receive the splines 34a and provide little clearance. In use, the drive surface of drive grooves 44c contact the splines 34a positioned within drive grooves 44c to rotate drive shaft 24. In a preferred embodiment, the drive grooves 44c and the guide grooves 44d alternate. However, this is not a limitation on the present invention. In the exemplary embodiment shown in the figures, the drive hub 18 includes three drive grooves 44c and three guide grooves 44d. However, this is not a limitation on the present invention and any number of drive grooves 44c and guide grooves 44d can be used.

In use, a new brushing attachment 14 is placed onto the brushing attachment connection receiver 22 such that the spline drive 34 is received into upper recess 42. As the spline drive 34 enters the incline section 42b, if the drive shaft 24 is misaligned, as a result of the incline, the spline drive 34 will be guided inwardly until the axis of the drive shaft 24 is generally axial with the axis of the drive hub 18 and the spline drive 34 will enter the straight section 42a of upper recess 42. The individual splines 34a each enter a corresponding drive groove 44c or guide groove 44d. The attachment mechanism between the handle 12 and brushing attachment 14 is attached and the toothbrush is now ready for use. When the toothbrush 10 is used, motivating rotational force is transferred from the motor to the drive hub 18, which, as a result of the interaction of splines 34a and drive grooves 44c, imparts motivating rotational force to drive shaft 24. As a result of gearing 32, the motivating rotational force is translated 90 degrees from the drive shaft 24 and to cleaning member 30, for teeth cleaning.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further any specific numbers noted herein are only examples: alternative implementations may employ differing values or ranges.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A toothbrush comprising:
a brushing attachment that includes
a main body portion that includes a hollow neck and a head, wherein the neck includes an attachment opening and the head includes a cleaning member opening,
a drive shaft positioned in the neck, wherein the drive shaft includes a spline drive having a plurality of splines on one end and gearing on the opposite end, wherein the spline drive is positioned adjacent the attachment opening in the neck,
a cleaning member drive mechanism matingly engaged with the gearing on the drive shaft, and
a cleaning member extending through the cleaning member opening in the head and operatively associated with the cleaning member drive mechanism,
a handle that includes
a main body portion that houses a motor, and
a brushing attachment connection receiver extending upwardly from the main body portion that is at least partially received in the attachment opening in the brushing attachment, wherein the brushing attachment connection receiver includes a recess defined therein that receives a drive hub therein, wherein the drive hub includes a grooved recess, said grooved recess having a plurality of grooves, an incline section and a straight section with a smaller outer diameter than the outer diameter than said incline section, and wherein each of the grooves are defined by a circumferential incline surface and two non-circumferential incline surfaces;
wherein individual splines are received in individual grooves when said grooved recess receives the spline drive.

2. The toothbrush of claim 1 wherein the splines each having a distal end, and wherein the distal end of each spline includes an inclined surface.

3. The toothbrush of claim 2 wherein each spline includes two opposing longitudinally extending surfaces that taper toward the distal end thereof.

4. The toothbrush of claim 1 wherein the grooved recess includes at least one drive groove having an inner surface and at least one guide groove having an inner surface, wherein the guide groove is larger in volume than the drive groove.

5. The toothbrush of claim 4 wherein the grooved recess includes a plurality of alternating drive grooves and guide grooves.

* * * * *